United States Patent
Rockwood et al.

(10) Patent No.: US 9,375,407 B2
(45) Date of Patent: Jun. 28, 2016

(54) DIMETHYL TRISULFIDE AS A CYANIDE ANTIDOTE

(71) Applicants: Gary A. Rockwood, Baltimore, MD (US); Ilona Petrikovics, Huntsville, TX (US)

(72) Inventors: Gary A. Rockwood, Baltimore, MD (US); Ilona Petrikovics, Huntsville, TX (US); Steven I. Baskin, Huntsville, TX (US)

(73) Assignees: Sam Houston State University, Huntsville, TX (US); U.S. Army, Secretary of the Army, Washington, DC (US)

( * ) Notice: Subject to any disclaimer, the term of this patent is extended or adjusted under 35 U.S.C. 154(b) by 0 days.

(21) Appl. No.: 14/685,008

(22) Filed: Apr. 13, 2015

(65) Prior Publication Data

US 2015/0290143 A1    Oct. 15, 2015

Related U.S. Application Data

(60) Provisional application No. 61/978,501, filed on Apr. 11, 2014.

(51) Int. Cl.
*A61K 31/105* (2006.01)
(52) U.S. Cl.
CPC .................................. *A61K 31/105* (2013.01)
(58) Field of Classification Search
CPC ................................................... A61K 31/105
See application file for complete search history.

(56) References Cited

U.S. PATENT DOCUMENTS

| | | |
|---|---|---|
| 4,292,311 A | 9/1981 | Sarnoff |
| 2014/0120159 A1 | 5/2014 | Petrikovics et al. |

FOREIGN PATENT DOCUMENTS

WO    2011/133893    10/2011

OTHER PUBLICATIONS

Cardiofy Website—www.cardiofy.com/plant_phytochemistry.htm, downloaded Jul. 17, 2012.
Zottola et al. "Disulfides as Cyanide Antidotes: Evidence for a New In Vivo Oxidative Pathway for Cyanide Detoxification" Chem. Res. Toxicol. 2009, 22, 1948-1953.
Bhattacharya "Antidotes to Cyanide Poisoning: Present Status" Indian Journal of Pharmacology 2000; 32: 94-101.
Iciek et al. "Allyl disulfide as donor and cyanide as acceptor of sulfane sulfur in the mouse tissues" Pharmacology Report 57, 212-218.
Frankenberg et al. "Enzyme therapy in cyanide poisoning: Effect of rhodanese and sulfur compounds" Archives of Toxicology, Oct. 1980, vol. 45, Issue 4, pp. 315-323.
Petrikovics Developement and Efficacy Testing of Next Generation Cyanide Antidotes, Annual Report for US Army Medical Research and Material Command, Award Number: w81XWH-12-2-0126, pp. 1-85, Oct. 2013.
Kovacs "Identification, Solubility Enhancement and in vivo Testing of a Cyanide Antidote Candidate" European Journal of Pharmaceutical Sciences, (2013), 49, 352-358.
International Search Report / Written Opinion for PCT Application No. PCT/US2015/025525 issued Jul. 8, 2015.
International Search Report / Written Opinion for PCT Application No. PCT/US2015/025528 issued Jul. 8, 2015.

*Primary Examiner* — Zohreh Fay
(74) *Attorney, Agent, or Firm* — Meyertons, Hood, Kivlin, Kowert & Goetzel, P.C.; Eric B. Meyertons

(57) ABSTRACT

Dimethyl trisulfide (DMTS) antidote compositions may be used to as a cyanide poisoning antidote.

9 Claims, 1 Drawing Sheet

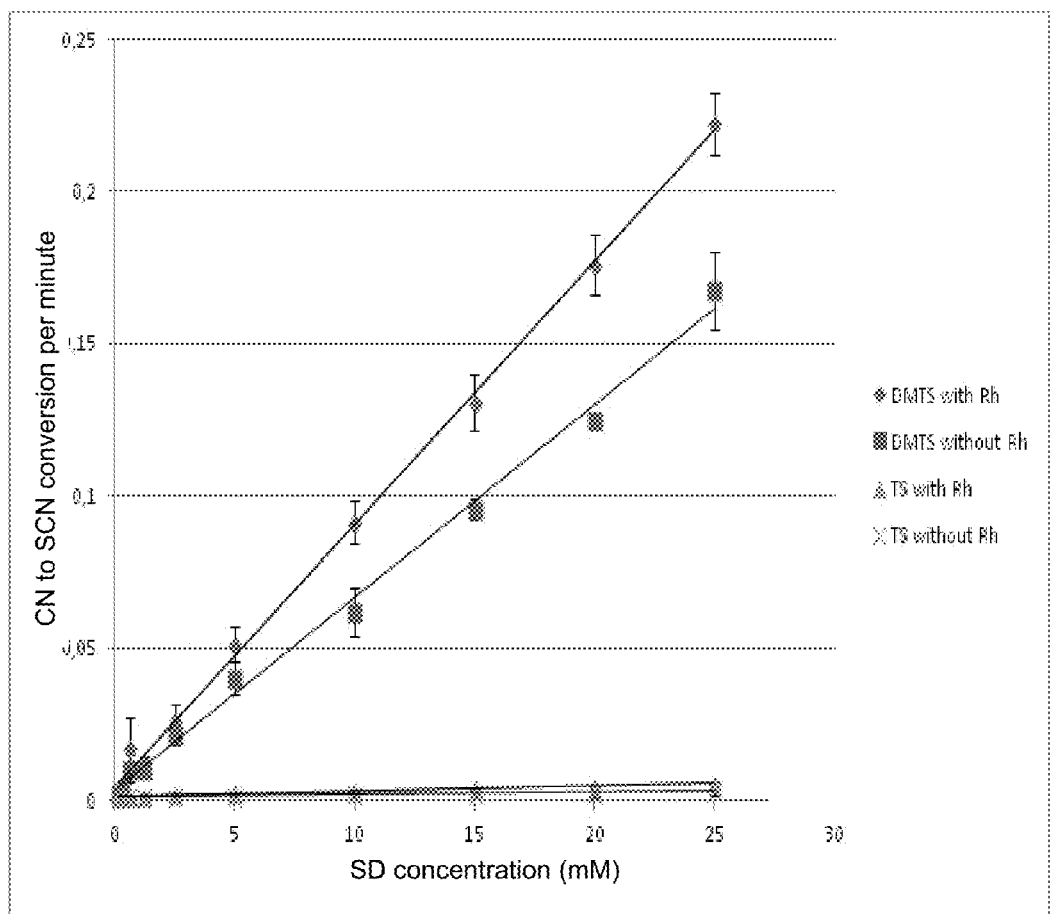

DIMETHYL TRISULFIDE AS A CYANIDE ANTIDOTE

PRIORITY CLAIM

This application claims priority to U.S. Provisional Application Ser. No. 61/978,501 entitled "DIMETHYL TRISULFIDE AS A CYANIDE ANTIDOTE" filed Apr. 11, 2014, which is incorporated herein by reference in its entirety.

BACKGROUND

1. Field of the Invention

The present invention relates to antidotes for blood agents. More particularly, the invention relates to cyanide antidotes.

2. Brief Description of the Related Art

Cyanide (CN) intoxication in humans can occur in a number of scenarios including as part of a chemical weapon-based military conflict. CN causes rapid and extensive cellular hypoxia through the binding of the ferric ($Fe^{3+}$) iron in the cytochrome c oxidase system leading to the collapse of the electron transport chain and thereby inhibiting the efficiency of oxygen transport to the tissues. Common cyanide compounds include hydrogen cyanide gas, cyanogen chloride gas, and crystalline solids such as potassium cyanide and sodium cyanide. The ease of delivery of these agents (especially gaseous cyanides) allow them to be used as an attack agent in chemical warfare.

Therapeutic attempts to counteract cyanide poisoning have been developed to inhibit the toxic effects of cyanide. For example, oxygen, sodium thiosulfate, amyl nitrite, sodium nitrite, 4-dimethylaminophenol, hydroxocobalamin, dicobalt EDTA, garlic extracts, disulfides, sodium pyruvate, alpha-keto-glutaric acid, aqueous solutions of ferrous sulfate in a citric acid sodium carbonate solution have been used for cyanide detoxification.

Presently in the United States two kits have been accepted as the standard of care. One is based on the intravenous administration of a combination of sodium nitrite and sodium thiosulfate (TS) (Nithiodote®), while the other intravenously used preparation contains hydroxocobalamin (Cyanokit®). Hydroxocobalamin binds to CN and forms cyanocobalamin, which is then excreted in the urine. Sodium nitrite leads to the formation of methemoglobin which has high affinity to CN and forms a relative stable complex of cyanomethemoglobin. Acting as a sulfur donor, TS helps bolster the natural CN detoxification by endogenous sulfur transferases, such as rhodanese (Rh), which utilize sulfur and convert CN into thiocyanate.

U.S. Pat. No. 4,565,311 to Samoff, which is incorporated herein by reference, describes as an antidote for cyanide poisoning injectable hydroxylamine hydrochloride. This is followed by treatment with thiosulfate. The hydroxylamine hydrochloride can also be employed as a respiratory stimulant in treating other illnesses.

Zottola et al. in "Disulfides as Cyanide Antidotes: Evidence for a New In Vivo Oxidative Pathway for Cyanide Detoxification." Chemical Research Toxicology, 2009, 22, pp. 1948-1953, which is incorporated herein by reference, describes the conversion of cyanide to thiocyanate (SCN) in the presence of the enzyme rhodanese. Rhodanese is an enzyme found primarily in the mitochondria. In a mammal, rhodanese is thought to be primarily responsible for the conversion of cyanide to SCN. Thiocyanate is then excreted by the kidney. Oxidized sulfur species such as sodium thiosulfate have been shown to be effective in vitro donors for rhodanese, however sodium thiosulfate in vivo efficacy is highly limited due to its limited cell penetration capability to reach the endogenous rhodanese. Thus, more effective sulfur analogs are desired.

The present therapies of sodium thiosulfate (TS) and sodium nitrite (SN) (Nithiodote®), and the hydroxocobalamin (Cyanokit®) both have limitations of requiring intravenous administration. Additionally, TS is highly dependent on the presence of sulfurtransferase enzyme (Rhodanese), and cannot easily penetrate through the mitochondrial membrane to reach the endogenous Rhodanese. The Cyanokit® requires high volume of administration to reach the required dose. There is, therefore, a need to develop a new, fast acting cyanide antidote that can be administered in a way that provides rapid absorption to protect individuals without requiring specialized techniques such as intravenous injection.

SUMMARY

Cyanide antidote methods are described herein. In some embodiments, a method of treating cyanide intoxication in a subject comprises administrating to a subject who would benefit from such treatment a therapeutically effective amount of dimethyl trisulfide (DMTS). The DMTS may be administered as a solution via intramuscular injection.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1 depicts a comparison of sulfur donor reactivity of DMTS vs the present therapy of Sodium thiosulfate (TS) in the presence and absence of the sulfurtransferase enzyme, rhodanese (Rh).

While the invention is susceptible to various modifications and alternative forms, specific embodiments thereof are shown by way of example in the drawing and will herein be described in detail. The drawing may not be to scale. It should be understood that the drawing and detailed description thereto is not intended to limit the invention to the particular form disclosed, but to the contrary, the intention is to cover all modifications, equivalents and alternatives falling within the spirit and scope of the present invention as defined by the appended claims.

DETAILED DESCRIPTION

It is to be understood that the present embodiments are not limited to particular compounds, methods or biological systems, which may, of course, vary. It is also to be understood that, as used in this specification and the appended claims, the singular forms "a", "an", and "the" include singular and plural referents unless the content clearly dictates otherwise. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below or elsewhere in the specification, to provide additional guidance to the practitioner in describing the general embodiments of the invention, as well as how to make and use them. It will be readily appreciated that the same thing can be said in more than one way.

Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, phrases such as "one or more additional compositions or medicaments suitable for the treatment of the toxic effects of cyanide in a subject," or more simply, "one or more additional compositions or medicaments," generally refer to a pharmaceutical composition that contains at least one pharmaceutically active compound that is used for the treatment of the toxic effects of cyanide in a subject, but which is distinct from the sulfur analogs or derivatives that form the basis of the present disclosure.

As used herein "cyanide intoxication" is to be understood to mean a medical condition that is characterized by cyanide interference with the performance of the cytochrome oxidase system thereby inhibiting the efficiency of oxygen transport to the tissues.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein the terms "administration," "administering," or the like, when used in the context of providing a pharmaceutical or nutraceutical composition to a subject generally refers to providing to the subject one or more pharmaceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, intra-osseous, transdermal, or buccal routes of delivery. Alternatively, or concurrently, administration may be by the oral route. The dosage administered will be dependent upon the age, health, weight, and/or intoxicated state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the terms "subject" generally refers to a mammal, and in particular to a human.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal has been exposed to cyanide and that may be detoxified, ameliorated, or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

The term "pharmacologically inert," as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

A method of treating cyanide intoxication in a subject includes administering to a subject who would benefit from such treatment a therapeutically effective amount of dimethyl trisulfide (DMTS). DMTS is a pale yellow clear oily liquid with a melting point of 58° C. at 15 mmHg. It is insoluble in aqueous solvents (solubility=0.13 mg/ml in distilled water) but soluble in most organic solvents. It is widely distributed in nature and is used as an FDA approved food flavoring/fragrance agent in food industry. To our knowledge, DMTS has not been used for the treatment of cyanide intoxication. The amount of DMTS administered is sufficient to convert at least some cyanide ions in the subject to SCN. The SCN may be excreted by the subject's kidney system.

In some embodiments, uses of dimethyl trisulfide, directed to treating cyanide intoxication in a subject, may include the preparation of pharmaceutical compositions for use with additional compounds which, when co-administered, act synergistically to convert cyanide to thiocyanate in a subject. Exemplary additional compounds that may be administered with DMTS include, but are not limited to sodium thiosulfate (TS), sodium nitrite (SN), hydroxocobolamin, and purified recombinant rhodanese.

One or more of the additional compounds suitable for the treatment of the cyanide intoxication presently contemplated may be formulated as a separate pharmaceutical composition to be administered in conjunction with the subject sulfur analogs as part of a therapeutic regimen, or may be formulated in a single preparation together with the sulfur analog.

Cyanide poisoning can cause death quickly in the victims that ingest, inhale, or even come into contact with substances that produce systemic cyanide poisoning in the victim. Death from cyanide poisoning can occur in less than 24 hours, generally 2-6 hours depending how the cyanide was administered, and the amount of cyanide the victim was exposed to. For the treatment of cyanide poisoning it is therefore important to be able to administer an effective detoxification agent quickly. Most commercially available cyanide poisoning treatments are designed for intravenous injection. While intravenous injection allows rapid delivery of the detoxification agent, it requires a skilled person to administer properly. It is important to have an administration method that is suitable for a large untrained population. Intramuscular or subcutaneous administration would achieve this goal, since the injection site would not be critical. In some embodiments, the injection may be administered into the muscle of the patient (i.e., intramuscular injection). In another embodiment, DMTS may be administered by subcutaneous injection.

Therapeutic kits that include dimethyl trisulfide are also contemplated herein. Such kits will generally contain, in suitable container, a pharmaceutically acceptable formulation of dimethyl trisulfide. The kits also may contain other pharmaceutically acceptable formulations, such as those containing components to target the dimethyl trisulfide to distinct regions of a patient where treatment is needed as well as appropriate devices for delivery of the dimethyl sulfide to the subject (e.g., an injection device).

The kits may have a single container that contains the DMTS, with or without any additional compositions or medicaments, or they may have distinct container means for each desired composition. When the components of the kit are provided in one or more liquid solutions, the liquid solution may be an aqueous solution, with a sterile buffered aqueous solution being particularly preferred. The container of the kit will generally include at least one vial, test tube, flask, bottle, syringe or other container, into which the dimethyl trisulfide, and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a device to administer the pharmaceutical compositions to an animal or patient, e.g., one or more needles or syringes, or even an eye dropper, or other such like apparatus, from which the formulation may be injected into the animal/human. The kits may also include a means for containing the vials, or such like, and other component, in close confinement for commercial sale, such as, e.g., injection or blow-molded plastic containers into which the desired vials and other apparatus are placed and retained.

Non-limiting examples of DMTS testing are described herein.

Example

Method for In Vitro Efficacy Determination

The conversion of KCN to potassium thiocyanate (KSCN) by dimethyl trisulfide (DMTS) was measured spectrophotometrically (Genesys 10UV, Thermo Electron Corporation, Waltham, Mass.). Briefly, 200 µl of various concentrations of DMTS in ethanol, 200 µl of 10 mM phosphate buffered saline, 200 µl of 250 mM KCN and 400 µl of deionized water were mixed. In the case of efficacy testing in the presence of Rh, 5 µl of 1 mg/mL of Rh solution (161 units/ml, one unit of Rh is defined to convert one micromole of CN to SCN per min at pH 8.6, at 25° C.) was added to the mixture at the start of the experiment replacing 5 µl of deionized water. After incubating for five minutes, the reaction was arrested by adding 500 µl of 15% (v/v) formaldehyde and colorized with 1.5 ml of ferric nitrate reagent. The color development was monitored at OD464 nm. Tests were performed with concentrations ranging from 25 mM to 0.156 mM with two fold serial dilutions in between and the results are presented at each data point as the average of triplicate assays. The results of these tests, for DMTS and TS are shown in FIG. 1.

Method for In Vivo Antidotal Efficacy Determination in a Mouse Model

Animal studies were conducted as therapeutic experiments using the Dixon up-and-down method for LD50 determination (Dixon, W. J., 1965. The up-and-down method for small animal samples. Am. Stat. Assoc. J. 12, 967-978) and the estimated 95% confidence interval was determined by the method of Bruce (Bruce R. D. 1985. An Up-and-Down procedure for acute toxicity testing. Fundam Appl Toxicol. 5:15-157.). Based on the weight of the animal an initial dose of KCN was injected subcutaneously from the KCN stock solution. Within 30 seconds, a predetermined dose (either 25 mg/kg, 50 mg/kg, 100 mg/kg or 200 mg/kg) of DMTS alone or in combination with sodium thiosulfate/magnesium thiosulfate (TS) was administered intramuscularly into the rear right leg of the mouse. The mice were then inspected and determined to be alive or dead. Based on the observation, a higher or a lower dose of KCN was injected in the following stage. This was repeated until enough data was collected to determine the LD50 values, and the program declared that the stopping condition has been met (i.e., four dose reversals). For each LD50 determination, 9-14 animals were used.

In Vivo Antidotal Efficacy of DMTS Vs TS

TABLE 1

Antidotal Potency Ratios for DMTS vs TS

| Exp # | Treatments | APR* |
|---|---|---|
| 1 | DMTS (50 mg/kg) (intramuscular) | 2.04 |
| 2 | DMTS (100 mg/kg) (intramuscular) | 3.4 |
| 3 | DMTS (200 mg/kg) (intramuscular) | 4.1 |
| 4 | TS (100 mg/kg) (intramuscular) | 1.1 |
| 5 | TS (200 mg/kg) (intramuscular) | 1.3 |

*APR = LD50 of CN with antidote/LD50 of CN without antidote

As it is seen on FIG. 1 and in Table 1, DMTS is superior to the present therapy of TS both in vitro and in vivo, and it has all the advantages that would make it a potential therapeutic agent to combat cyanide intoxication. In the form of an intramuscular kit it would be suitable even for a mass scenario.

In Vivo Antidotal Efficacy of the DMTS+TS/SN Combinations

The in vivo efficacy tests for DMTS TS/SN combinations were run the same way as described above according to the standard protocol. Results are presented in Table 2.

TABLE 2

In vivo efficacy with the combinations of DMTS with TS and/or SN.

| Antidotes | Treatments/Doses of Antidotes (im) | APR* |
|---|---|---|
| DMTS | DMTS (12.5 mg/kg) | 2.1 |
| DMTS | DMTS (25 mg/kg) | 1.7 |
| DMTS | DMTS (50 mg/kg) | 2.0 |
| DMTS | DMTS (100 mg/kg) | 3.4 |
| DMTS | DMTS (200 mg/kg) | 4.1 |
| DMTS | DMTS (100 mg/kg) | 3.2 |
| TS | TS (100 mg/kg) (im) | 1.1 |
| TS | TS (200 mg/kg) (im) | 1.3 |
| DMTS + TS | DMTS (25 mg/kg) + TS (200 mg/kg) | 2.1 |
| DMTS + TS | DMTS (50 mg/kg) + TS (200 mg/kg) | 2.8 |
| DMTS + TS | DMTS (100 mg/kg) + TS (200 mg/kg) | 4.6 |
| SN | SN (3.2 mg/kg) | 1.0 |
| SN | SN (6.4 mg/kg) | 1.3 |
| DMTS + SN | DMTS (50 mg/kg) + SN (3.2 mg/kg) | 2.1 |
| DMTS + SN | DMTS (50 mg/kg) + SN (6.4 mg/kg) | 2.9 |
| DMTS + TS + SN | DMTS (25 mg/kg) TS (200 mg/kg) SN (6.4 mg/kg) | 2.6 |
| DMTS + TS + SN | DMTS (50 mg/kg) TS (200 mg/kg) SN (6.4 mg/kg) | 2.8 |

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims

What is claimed is:

1. A method of treating cyanide intoxication in a subject, comprising:
    administrating to a subject who would benefit from such treatment a therapeutically effective amount of dimethyl trisulfide (DMTS).

2. The method of claim 1, wherein the DMTS is administered transdermally.

3. The method of claim 1, wherein the DMTS is administered via an aerosol delivery system.

4. The method of claim 1, wherein the DMTS is administered intramuscularly.

5. The method of claim 1, wherein the DMTS is administered subcutaneously.

6. The method of claim 1, wherein the DMTS is administered intra-osseously.

7. The method of claim 1, wherein the DMTS is administered sublingually.

8. The method of claim 1, wherein the DMTS is administered as an eye drop in a solution.

9. The method of claim 1, wherein the DMTS is administered as a rectal administration via a rectal delivery system.

* * * * *